United States Patent [19]

Richter

[11] 4,020,104

[45] Apr. 26, 1977

[54] PROCESS FOR ISOMERIZING CIS,CIS- AND CIS,TRANS-ISOMERS OF DI-(P-AMINOCYCLOHEXYL)METHANE TO THE CORRESPONDING TRANS,TRANS-ISOMER

[75] Inventor: Reinhard H. Richter, North Haven, Conn.

[73] Assignee: The Upjohn Company, Kalamazoo, Mich.

[22] Filed: Sept. 20, 1976

[21] Appl. No.: 724,585

[52] U.S. Cl. .......................... 260/563 B; 260/566 F
[51] Int. Cl.$^2$ ................... C07C 85/18; C07C 85/20
[58] Field of Search ..................... 260/563 B, 566 F

[56] References Cited

UNITED STATES PATENTS 3,856,862  12/1974  Chung et al. ................. 260/563 B

FOREIGN PATENTS OR APPLICATIONS 725,875  3/1955  United Kingdom ............ 260/563 B Primary Examiner—Gerald A. Schwartz
Attorney, Agent, or Firm—Denis A. Firth; John Kekich

[57] ABSTRACT

A process is described for isomerizing the cis,cis- and cis,trans-isomers of di-(p-aminocyclohexyl)methane to the corresponding trans,trans-isomer. The starting isomer, or mixture of isomers, is converted to the corresponding bis-benzaldimine by reaction with benzaldehyde (or benzaldehyde containing 1 to 3 inert substituents), the bis-benzaldimine is isomerized in the presence of a basic catalyst (potassium t-butoxide, potassium hydroxide preferred) to give predominantly the trans,trans-isomer of the bis-benzaldimine, and the latter is subjected to acid hydrolysis to yield the trans,-trans-isomer of the free diamine. The process can be applied to the individual cis,cis- and cis,trans-isomers of the diamine as well as to admixtures of these isomers with the trans,trans-isomer, such as the mixtures of these stereoisomers obtained by catalytic hydrogenation of di-(p-aminophenyl)methane.

7 Claims, No Drawings

PROCESS FOR ISOMERIZING CIS,CIS- AND CIS,TRANS-ISOMERS OF DI-(P-AMINOCYCLOHEXYL)METHANE TO THE CORRESPONDING TRANS,TRANS-ISOMER

BACKGROUND OF THE INVENTION

1. Field of the Invention

This invention relates to methods of isomerizing the stereoisomers of cycloaliphatic diamines and is more particularly concerned with producing di-(p-aminocyclohexyl)methane rich in trans,trans-isomer.

2. Description of the Prior Art

Di-(p-aminocyclohexyl)methane is generally prepared by the catalytic hydrogenation of di-(p-aminophenyl)methane; see, for example, U.S. Pat. Nos. 2,494,563; 2,606,924; 2,606,928; 3,591,635 and 3,856,862. The products so obtained are found to be mixtures of the various possible stereoisomers, namely, the cis,cis-, cis,trans- and trans,trans-isomers.

For many purposes it is desirable to employ the substantially pure trans,trans-isomer. For example, polyamides derived from the latter isomer and dibasic aliphatic and aromatic carboxylic acids produce synthetic fibers having highly desirable properties; see, for example, Tedder et al., Basic Organic Chemistry, Part 5, pp. 283–4, John Wiley and Sons, London, 1975. Various methods have been reported for the separation of the stereoisomers one from another but it is obviously much more desirable from an economic standpoint to be able to convert the cis,cis- and cis,trans-isomers to the trans,trans-isomer. Such isomerization has been accomplished hitherto by subjecting the mixture of isomers to high temperature in the presence of catalysts; see, for example, Japan 71/30,835, Japan 71/16,979, German No. 1,768,427 and German Offen. 2,301,106. This method, in addition to the disadvantages of using high temperatures, results in significant overall loss of the diamine due to side reactions.

I have now found that the above isomerization can be effected readily, in substantially quantitative yield and without the use of elevated temperatures, by the process which is described below.

SUMMARY OF THE INVENTION

This invention comprises a process for the isomerization of the cis,cis- and or cis,trans-isomers of di-(p-aminocyclohexyl)methane to form predominantly the corresponding trans,trans-isomer which comprises reacting said stereoisimers of di-(p-aminocyclohexyl)methane with at least a stoichiometric amount of a benzaldehyde of the formula:

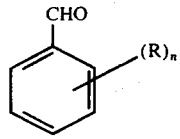
(I)

wherein $n$ is an integer from 0 to 3 and R is an inert substituent, to form the corresponding bis-benzaldimine of di-(p-aminocyclohexyl)methane;

contacting said bis-benzaldimine with a base in an inert organic solvent at ambient temperature to effect isomerization of the cis,cis- and cis,trans-isomers of said bis-benzaldimine to the corresponding trans,trans-isomer; and subjecting the resulting product to acid hydrolysis to yield di-(p-aminocyclohexyl)methane enriched in trans,trans-isomer.

The process of the invention can be applied to the isolated cis,cis-isomer and the isolated cis,trans-isomer as well as to mixtures of said isomers alone or in combination with the trans,trans-isomer.

The invention also comprises the novel bis-benzaldimines of the various stereoisomers of di-(p-aminocyclohexyl)methane.

The term "inert substituent" as used herein in the specification and claims means a substituent which does not enter into reaction with the other components of the reaction mixture employed in the process of the invention or in any way interfere with the desired course of the reaction. Examples of such substituents are lower-alkyl, i.e. alkyl from 1 to 6 carbon atoms, inclusive, such as methyl, ethyl, propyl, butyl, pentyl, hexyl and isomeric forms thereof; lower-alkoxy, i.e. alkoxy from 1 to 6 carbon atoms, inclusive, such as methoxy, ethoxy, propoxy, butoxy, pentyloxy, hexyloxy, and isomeric forms thereof; dialkylamino, wherein each alkyl group is lower-alkyl as above defined, such as dimethylamino, diethylamino, dihexylamino, N-methyl-N-butylamino, and the like; halogen, i.e. chlorine, bromine, fluorine, iodine; and lower-alkyl-mercapto, i.e. alkylmercapto from 1 to 6 carbon atoms, inclusive, such as methylmercapto, ethylmercapto, propylmercapto, butylmercapto, pentylmercapto, hexylmercapto, and isomeric forms thereof.

DETAILED DESCRIPTION OF THE INVENTION

In carrying out the process of the invention there can be used as the starting material the individual cis,cis- and cis,trans-isomers of the di-(p-aminocyclohexyl)methane (II) or mixtures of these isomers with each other as well as with the trans,trans-isomer. Thus, in a particular embodiment, the process of the invention is employed to convert the cis,cis- and cis,trans-isomers, present in admixture with the trans,trans-isomer, in the product obtained by catalytic hydrogenation of di-(p-aminophenyl)methane, to the trans,trans-isomer thereby producing a diamine (II) which is enriched in, or composed substantially of, the trans,trans-isomer.

In the first step of the process of the invention the diamine (II) which is to be isomerized, whether it be the individual cis,cis- or cis,trans-isomers or mixtures thereof with trans,trans-isomer, is converted to the corresponding bis-benzaldimine (III) by reaction with the appropriate benzaldehyde (I) under conditions well-known in the art for the formation of Schiff's bases; see, for example, Houben-Weyl-Müller, Methoden der organischen Chemie, 7/1, 453, 1954. The reaction is represented by the following equation:

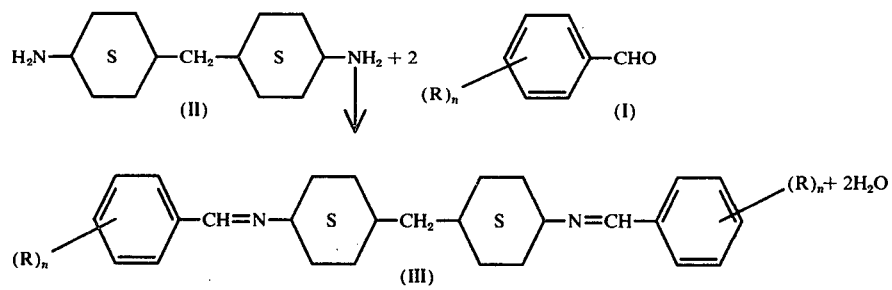

wherein R and *n* have the significance hereinbefore defined. Each of the stereoisomers present in the starting diamine (II) will give rise to the corresponding stereoisomer of the bis-benzaldimine (III).

Advantageously, the above reaction is carried out by bringing the diamine (II) and the benzaldehyde (I) together, organic solvent. By the latter is meant an organic solvent which does not react with either of the reactants or interfere in any other way with the desired course of the reaction. Illustrative of inert organic solvents are benzene, toluene, xylene, chlorobenzene, diethyl ether, tetrahydrofuran, dimethylsulfoxide, ethyl acetate, dimethylformamide, dimethylacetamide, and the like. The reaction is generally exothermic, proceeds very readily, and does not require the application of any external heat. Indeed, cooling of the reaction mixture may be necessary in certain cases to control the reaction.

The diamine (II) and the benzaldehyde (I) are employed in substantially stoichiometric proportions, i.e. 2 moles of the benzaldehyde (I) per mole of the diamine (II) but a slight excess of benzaldehyde (I) can be employed if desired. The water which is eliminated in the condensation is removed by distillation at the end of the reaction or while the reaction is in progress. The use of solvent such as benzene in the reaction facilitates the removal of the water of condensation as an azeotrope either during the reaction of after completion thereof.

The bis-benzaldimine (III) so obtained is generally a solid which remains as the residue after removal of water and solvent, if one has been used in the condensation. The bis-benzaldimine (III) can be purified by crystallization and like procedures, if desired, prior to use in the second step of the process of the invention. However, such purification is not essential and the product obtained from the above condensation can be used without further treatment in most cases.

Illustrative of benzaldehydes (I) which can be used in the above condensation are benzaldehyde, anisaldehyde, m-methoxybenzaldehyde, p-ethoxybenzaldehyde, p-butoxybenzaldehyde, p-hexyloxybenzaldehyde, 3,4-dimethoxybenzaldehyde, 3,4,5-trimethoxybenzaldehyde, m-tolualdehyde, p-ethylbenzaldehyde, m-butylbenzaldehyde, p-hexylbenzaldehyde, 3,4,5-trimethylbenzaldehyde, p-methylmercaptobenzaldehyde, p-butylmercaptobenzaldehyde, p-dimethylaminobenzaldehyde, p-diethylaminobenzaldehyde, 3-methyl-4-dimethylaminobenzaldehyde, p-chlorobenzaldehyde, m-fluorobenzaldehyde and the like.

In the second stage of the process of the invention the benzaldimine (III) is dissolved or suspended in an inert organic solvent and subjected to the action of a base at ambient temperature, i.e. temperatures in the range of about 15° to 30° C or at elevated temperatures up to about 60° C or even higher if desired. Illustrative of bases which are employed in this stage of the process are alkali metal hydroxides such as potassium hydroxide, lithium hydroxide, cesium hydroxide and the like; and alkali metal alkoxides such as potassium, lithium and cesium methoxides, ethoxides, t-butoxides and the like. Advantageously, the amount of said base employed is within the range of about 15 to about 100 mole percent based on bis-benzaldimine (III) and is preferably within the range of about 30 to about 50 mole percent based on bis-benzaldimine (III).

Illustrative of the organic solvents which are employed in the above isomerization stage of the reaction are ethers such as dimethoxyethane, tetrahydrofuran, the cyclic polyethylene ether known as 18-crown-6-ether, and analogues thereof in which one or more oxygen atoms are replaced by —NH— or bridging groups N+(CH$_2$)$_2$O]$_n$(CH$_2$)$_2$—N, dimethylsulfoxide, dimethylformamide, hexamethylphosphoramide, and the like. The cyclic polyethylene ethers, in combination with alkali metal hydroxides, especially potassium hydroxide, represent a preferred catalyst system. The treatment of the solution of the bis-benzaldimine (III) with the base is continued until the isomerization of the cis,cis- and cis,trans-isomers of the bis-benzaldimine (III) to the corresponding trans,trans-isomer is adjudged to be substantially complete. The latter point can be determined by subjecting aliquots of the reaction mixture to analysis by techniques such as $^{13}$C nuclear magnetic resonance spectroscopy.

The bis-benzaldimine (III) enriched in trans,trans-isomer can be isolated from the reaction product by conventional procedures, for example, by neutralization of the base catalyst followed by removal of the solvent. The product so obtained can be purified, if desired, by recrystallization and like procedures, before being subjected to the final stage of the process. In the latter, the bis-benzaldimine (III), which has been subjected to isomerization to yield a product rich in trans, trans-isomer, is hydrolyzed to liberate the free diamine (II), now rich in trans,trans-isomer. The hydrolysis is advantageously carried out using aqueous mineral acid such as hydrochloric, hydrobromic, sulfuric acids and the like. The acid is preferably employed in excess of the stoichiometric amount, i.e. in excess of two hydrolysis is advantageously conducted at slightly elevated temperature up to about 40° C or even higher in certain cases depending upon the ease of hydrolysis of the particular bis-benzaldimine.

The product so obtained is a mixture of the benzaldehyde (I) originally employed to prepare the bis-benzaldimine (III) and an aqueous solution of the acid salt of the diamine (II). The latter is isolated from its acid solution by neutralization of the latter with a base such as aqueous sodium or potassium hydroxide or carbonate. The diamine (II) so obtained is generally substantially pure trans,trans-isomer or is greatly enriched in the latter isomer as compared with the starting diamine (II) used in the process. The diamine (II) can be purified, if desired or if necessary, by recrystallization, chromatography and like techniques.

It is found that the recovery of diamine (II) and benzaldehyde (I) in this last stage of the process of the invention is substantially quantitative, based on the amounts of the starting materials used. The overall process results in no substantial loss of diamine (II). The benzaldehyde (I) recovered in the final stage of the process in substantially quantitative amount can be reused in a subsequent cycle of operations. The overall process of the invention is accordingly very economical to operate, does not involve extensive energy requirements, and does not require the disposal of large quantities of waste by-products.

The following examples describe the manner and process of making and using the invention and set forth the best mode contemplated by the inventor of carrying out the invention but are not to be construed as limiting.

EXAMPLE 1

A. Preparation of the bis-benzaldimine of a mixture of cis,cis-, cis,trans- and trans,trans-di-(p-aminocyclohexyl)methane A mixture of 21.0 g. (0.1 mole) of di-(p-aminocyclohexyl)methane [shown by $^{13}C$ nuclear magnetic resonance (NMR) spectroscopy to contain an overall cis-trans-isomer ratio of 72:28] and 21.2 g. (0.2 mole) of benzaldehyde in 100 ml. of benzene was heated under reflux using a Dean-Stark apparatus until no more water was eliminated in the azeotrope. The resulting solution was evaporated to dryness to leave, as a solid residue, the bis-benzaldimine of di-(p-aminocyclohexyl)methane in the form of a mixture of the cis,cis-, cis,trans- and trans,trans-isomers, the overall ratio of cis to trans being 72:28.

B. Isomerization of the stereoisomers of the bis-benzaldimine

To a mixture of 4.5 g. (0.012 mole) of the bis-benzaldimine prepared as described above and 35 ml. of dimethoxyethane maintained in an atmosphere of nitrogen was added, with stirring, 1.2 g. (0.01 mole) of potassium t-butoxide and the stirring was continued until a nearly homogenous solution was obtained. The resulting solution was allowed to stand in an atmosphere of nitrogen for 42 hours at room temperature (circa 20° C). At the end of this time the solvent was removed by distillation using a rotary evaporator and the residue was triturated with 50 ml. of water. The resulting mixture was extracted with chloroform. The chloroform extract was washed with water, dried over anhydrous magnesium sulfate and evaporated to dryness. The residue (4.5 g.) of bis-benzaldimine was found, by examination of an aliquot (dissolved in CDCl$_3$) by $^{13}C$ NMR spectroscopy, to contain an overall cis- to trans-isomer ratio of 16:84.

EXAMPLE 2

This example shows a repetition of the process of Example 1, Part B, using a longer reaction time.

To a mixture of 10 g. (0.026 mole) of the bis-benzaldimine prepared as described in Example 1, Part A, and 20 ml. of dimethoxyethane, maintained under atmosphere of nitrogen, was added, with stirring, 2.0 g. (0.018 mole) of potassium t-butoxide. The mixture was stirred at room temperature (circa 20° C) under an atmosphere of nitrogen for 4 to 5 hours and was then allowed to stand for a total of 40 hours from the time of mixing. The resulting suspension was evaporated to dryness using a rotary evaporator and the residue was triturated with water. The aqueous suspension was filtered, the solid precipitate was washed with water on the filter, and dried at 70° C. There was thus obtained 9.7 g. (97 percent recovery) of the bis-benzaldimine which was shown by $^{13}C$ NMR spectroscopy to be substantially pure trans,trans-isomer.

EXAMPLE 3

A suspension of 10 g. of the bis-benzaldimine (obtained by combining two runs from the isomerization described in Example 2 above) in a mixture of 20 ml. of conc. hydrochloric acid and 80 ml. of water, was heated with stirring at circa 50° C for 30 minutes. The resulting product was cooled to room temperature and extracted with four portions, each of 10 ml., of methylene chloride. The combined extracts were dried over anhydrous magnesium sulfate and evaporated to dryness to obtain 5.85 g. of benzaldehyde. The acidic solution, after extraction with methylene chloride as described above, was made alkaline by the addition of 50 ml. of 30 percent w/w aqueous sodium hydroxide solution. The mixture so obtained was extracted with five 10 ml. portions of methylene chloride and the combined extracts were washed with water and dried over anhydrous sodium sulfate. The dried extract was evaporated to dryness to yield 5.5 g. (100 percent recovery) of di-(p-aminocyclohexyl)methane. The latter was shown, by $^{13}C$ NMR spectroscopy, to be substantially pure trans,trans-isomer.

EXAMPLE 4

A mixture of 5 g. (0.013 mole) of the bis-benzaldimine prepared as described in Example 1, Part A, 10 ml. of dimethoxyethane, 0.2 g. of 18-crown-6 [cyclic poly(oxyethylene): Parish Chemical Company, Provo, Utah] and 1 g. (0.018 mole) of powdered potassium hydroxide was stirred for 24 hours at room temperature (circa 20° C). The resulting mixture was allowed to stand for a further 71 hours at the same temperature before evaporating the solvent and triturating the residue with water. The solid material was isolated by filtration, washed with water and dried at 70° C. There was thus obtained a quantitative yield of the bis-benzaldimine which was shown, by $^{13}C$ NMR spectroscopy, to have trans,trans-isomer content of greater than 95 percent by weight.

The above bis-benzaldimine was hydrolyzed using the procedure described in Example 3 to recover the corresponding trans,trans-di-(p-aminocyclohexyl)methane in substantially quantitive yield.

EXAMPLE 5

The process of Example 4 was repeated exactly as described except that the 0.2 g. of 18-crown-6 was replaced by 0.1 g. of diaza-18-crown-6 (1,7,10,16-tetraoxa-4,13-diazacylooctadecane: Kryptofix 22; Parish Chemical Company, Provo, Utah). There was thus obtained a quantitative yield of bis-benzaldimine which was shown, by $^{13}$C NMR spectroscopy, to be substantially pure trans,trans-isomer.

I claim:

1. A process for the isomerization of the cis-cis- and cis,trans-isomers of di-(p-aminocyclohexyl)methane to form predominantly the corresponding trans,trans-isomer which comprises reacting said stereoisomers of di-(p-aminocyclohexyl)methane with a benzaldehyde of the formula:

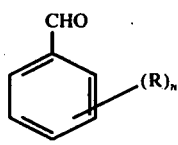

wherein $n$ is an integer from 0 to 3 is an inert substituent to form the corresponding bis-benzaldimine of di-(p-aminocyclohexyl)methane;

contacting said bis-benzaldimine with a base in a polar solvent at ambient temperature to effect isomerization of the cis,cis- and cis,trans-isomers of said bis-benzaldimine to the corresponding trans,trans-isomer; and subjecting the resulting product to acid hydrolysis to yield di-(p-aminocyclohexyl)methane enriched in trans,trans-isomer.

2. The process of claim 1 wherein said base is potassium t-butoxide.

3. The process of claim 1 wherein said base is potassium hydroxide in the presence of 18-crown-6-ether.

4. The process of claim 1 wherein benzaldehyde is employed in the preparation of said bis-benzaldimine.

5. A process which comprises isomerizing a stereoisomer selected from the cis,cis- and cis,trans-isomers of di-(p-aminocyclohexyl)methane bis-benzaldimine and mixtures thereof in the presence of a base to form the corresponding bis-benzaldimine.

6. The process of claim 5 wherein the base is potassium t-butoxide.

7. The process of claim 5 wherein the base is potassium hydroxide in the presence of 18-crown-6-ether.

* * * * *

UNITED STATES PATENT OFFICE
CERTIFICATE OF CORRECTION

Patent No. 4,020,104　　　　　　　　　Dated April 26, 1977

Inventor(s) Reinhard H. Richter

It is certified that error appears in the above-identified patent and that said Letters Patent are hereby corrected as shown below:

Column 3, line 21:

together, organic solvent.

Should read:

together, optionally, but not necessarily, in the presence of an inert organic solvent.

Column 4, line 33:

$N + (CH_2)_2 O]_n (CH_2)_2 - N$

Should read:

$N + (CH_2)_2 O \frac{1}{n} (CH_2)_2 - N$

Column 4, line 61:

two hydrolysis

Should read:

two equivalents of acid per mole of bis-benzaldimine. The hydrolysis

Column 7, Claim 1, line 18:

0 to 3 is

Should read:

0 to 3 and R is

UNITED STATES PATENT OFFICE
CERTIFICATE OF CORRECTION

Patent No. 4,020,104                    Dated   April 26, 1977

Inventor(s)   Reinhard H. Richter

It is certified that error appears in the above-identified patent and that said Letters Patent are hereby corrected as shown below:

Column 8, Claim 5, line 17            should read:

corresponding bis-benzaldimine.       corresponding trans,trans-isomer of said bis-benzaldimine.

Signed and Sealed this twelfth Day of July 1977

[SEAL]

Attest:

RUTH C. MASON
Attesting Officer

C. MARSHALL DANN
Commissioner of Patents and Trademarks